(12) United States Patent
Walter et al.

(10) Patent No.: US 10,345,198 B2
(45) Date of Patent: Jul. 9, 2019

(54) METHOD AND MICROTOME FOR PRODUCING THIN SECTIONS WITH A SECTION PROFILE RECORDING MODE

(71) Applicant: Leica Biosystems Nussloch GmbH, Nussloch (DE)

(72) Inventors: Roland Walter, Reilingen (DE); Markus Berberich, Heidelberg (DE); Markus Wittman, Heidelberg (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 0 days.

(21) Appl. No.: 15/026,000

(22) PCT Filed: Aug. 18, 2014

(86) PCT No.: PCT/EP2014/067537
§ 371 (c)(1),
(2) Date: Mar. 30, 2016

(87) PCT Pub. No.: WO2015/043831
PCT Pub. Date: Apr. 2, 2015

(65) Prior Publication Data
US 2016/0245728 A1    Aug. 25, 2016

(30) Foreign Application Priority Data
Sep. 30, 2013  (DE) .................. 10 2013 110 776

(51) Int. Cl.
*G01N 1/06* (2006.01)
*G01N 1/28* (2006.01)

(52) U.S. Cl.
CPC ............... *G01N 1/06* (2013.01); *G01N 1/286* (2013.01); *G01N 2001/065* (2013.01); *G01N 2001/066* (2013.01); *G01N 2001/2873* (2013.01)

(58) Field of Classification Search
CPC .. G01N 1/06; G01N 1/286; G01N 2001/2873; G01N 2001/065;
(Continued)

(56) References Cited

U.S. PATENT DOCUMENTS

| 5,226,335 A | 7/1993 | Sitte et al. |
| 5,253,653 A * | 10/1993 | Daigle .................. A61M 25/09 600/434 |

(Continued)

FOREIGN PATENT DOCUMENTS

| EP | 1037032 B1 | 9/2000 |
| WO | 91/15746 A1 | 10/1991 |

OTHER PUBLICATIONS

English Translation of WO9115746 (retrieved Feb. 22, 2018).

*Primary Examiner* — Ghassem Alie
(74) *Attorney, Agent, or Firm* — Hodgson Russ LLP

(57) ABSTRACT

A method of producing thin sections using a microtome is disclosed. A hand wheel (32) is manually driven for producing a first thin section, and wherein the rotational movement of the hand wheel (32) is detected by an encoder (38), and a profile of the rotational movement is determined. The determined profile is stored and selected for production of at least a second thin section. A motor (24) is driven for generating a cutting movement between a cutting unit (16) and a sample holder (12) in accordance with the respective stored profile selected for producing the second thin section. A microtome (10) to carry out this method is also disclosed.

10 Claims, 4 Drawing Sheets

(58) Field of Classification Search
CPC .... G01N 2001/066; B26D 5/08; B26D 5/086;
B26D 7/24; Y10T 83/18; Y10T 83/6492;
Y10T 83/9493; Y10T 83/6667
USPC ... 83/915.5, 703, 733, 856, 170, 403.1, 403,
83/410.8, 410.9, 411.3, 267
See application file for complete search history.

(56) References Cited

U.S. PATENT DOCUMENTS

| | | | |
|---|---|---|---|
| 6,598,507 B1 * | 7/2003 | Gunther | B26D 5/08 83/703 |
| 6,634,268 B1 | 10/2003 | Guenther et al. | |
| 2004/0149106 A1 * | 8/2004 | Hess | G01N 1/06 83/575 |
| 2010/0180742 A1 * | 7/2010 | Walter | G01N 1/06 83/399 |
| 2012/0240737 A1 | 9/2012 | Yang et al. | |

\* cited by examiner

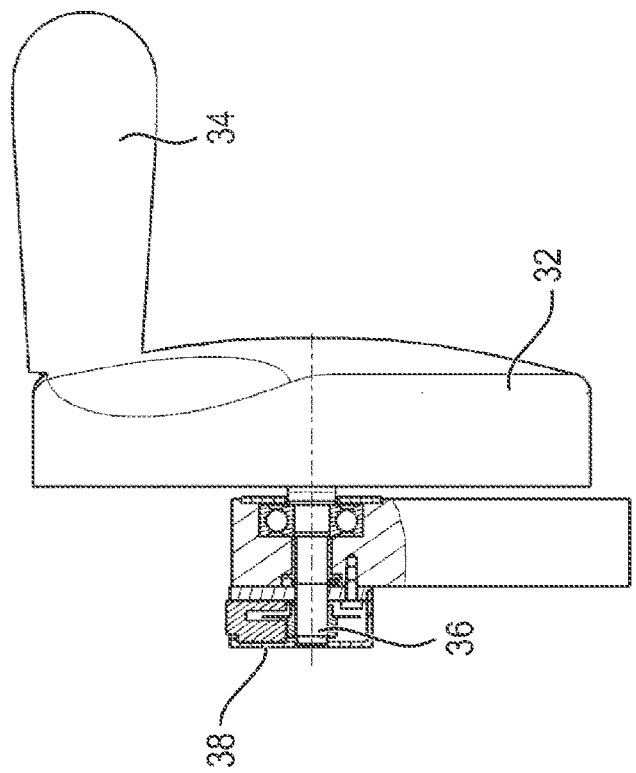
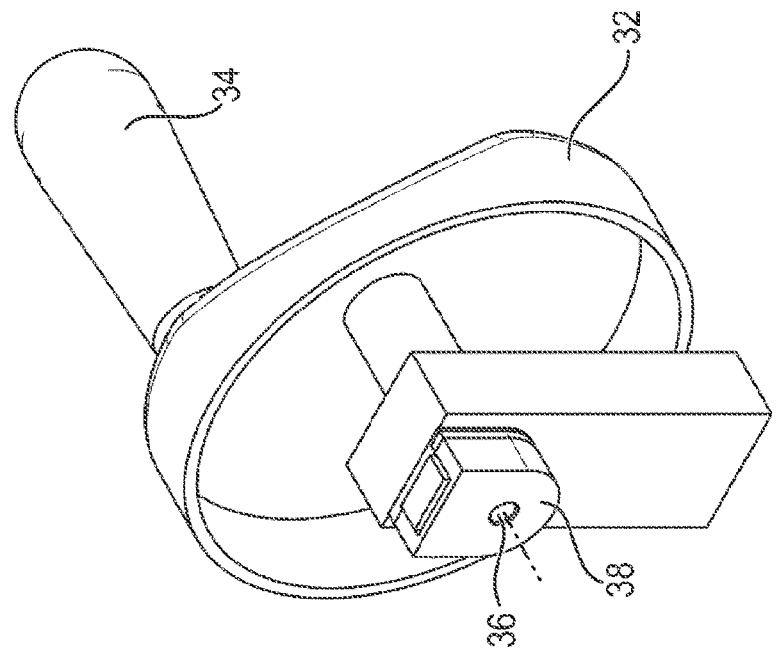
FIG. 4
FIG. 3

METHOD AND MICROTOME FOR PRODUCING THIN SECTIONS WITH A SECTION PROFILE RECORDING MODE

The present invention relates to a method of producing thin sections by means of a microtome wherein a hand wheel is manually driven for producing a first thin section, and wherein the rotational movement of the hand wheel during production of the first thin section is detected by means of an encoder, and a profile of the rotational movement is determined. The invention further relates to a microtome comprising a sample holder for receiving a sample to be microtomed, a cutting unit for cutting the sample, a motor for generating a relative movement between the sample holder and the cutting unit for cutting the sample, and a manually operable hand wheel. Further, the microtome has an encoder for detecting a rotational movement of the hand wheel, and a control unit for driving the motor.

Microtomes are used for producing thin sections of samples. The samples are in particular tissue samples which typically are embedded in paraffin prior to cutting. The paraffin block thus formed is clamped in the sample holder of the microtome before the thin sections are produced via relative movement between the sample holder and a cutting element. Then, the thin sections are placed on coverslips, and following further processing, such as staining, they are fed to a microscope for microscopic examination.

Depending on the type of the sample to be microtomed, different cutting speeds and accelerations during the cutting movement are required for obtaining good section quality and for preventing the sample from being damaged. Furthermore, a so-called cutting window has to be set depending on the sample size, said cutting window representing the range of the corresponding cutting speed and cutting acceleration required.

Microtomes are known wherein the relative movement between sample holder and cutting unit is automatically performed by means of a motor. In order to satisfy the needs of different types of samples, the cutting speed usually may be adjusted stepwise. For each speed level which can be set, such motor-driven microtomes often provide one predetermined cutting profile representing the progress of the cutting speed during production of a thin section. Usually, a drive shaft of the motor is driven at a constant speed, said constant speed being correspondingly transformed into a sinusoidal cutting speed profile by a crank mechanism. In particular, the reverse stroke may thus be performed at higher speeds.

A problem in such motor-driven microtomes is that control through an operator is restricted and that adaptation to the sample type is possible only via the preset cutting speeds to an insufficient extent. Moreover, manual adaptation to the respective sample is impossible. Furthermore, the cutting window must be manually set for each sample in a time-consuming manner.

Further, microtomes are known comprising a hand wheel which is mechanically connected to the sample holder via a crank mechanism, and thus serves for generating the cutting movement. The advantage of such manually-driven microtomes is that the operator may directly influence the cutting speed profile. The disadvantage, however, is that exact reproducibility of a cutting movement is impossible, and therefore uniform section quality cannot be guaranteed. Moreover, the operator must drive the hand wheel for each thin section.

From document EP 1 037 032 B1 there is known a microtome wherein the hand wheel is not mechanically coupled to the sample holder and the cutting element. The hand wheel is rather connected to an encoder detecting the rotational movement of the hand wheel and generating corresponding positional data. In accordance with the detected rotational movement, a motor moves the sample holder relative to the cutting unit in real-time. Thus, the same cutting movement is carried out as would be performed with mechanical coupling of hand wheel and cutting unit, or sample holder, respectively, although such mechanical coupling is not provided. Further, the disadvantage of microtomes of this type is that reproducibility of a cutting profile is not possible and that the operator must drive the hand wheel for production of each section.

It is an object of the present invention to provide a method and a microtome for producing thin sections by means of which high quality thin sections can be produced in a simple manner.

This object is achieved by a method having the features of claim 1 and by a microtome having the features of the independent device claim.

Advantageous developments of the invention are described in the dependent claims.

According to the invention, in a recording mode, the profile of the rotational movement of the hand wheel detected by means of the encoder during production of first thin section is stored in a storage element. Said stored profile can be selected for production of a second thin section, wherein a motor for generating the cutting movement between a cutting unit and a sample holder is driven in accordance with the selected stored profile for producing the second thin section.

In particular, the profile comprises information as to at which time the hand wheel was moved at which speed, thus characterizing the cutting movement correspondingly performed through the motor. It is achieved thereby that firstly, via manually driving the hand wheel when producing the first thin section, the ideal cutting profile for each type of sample can be used. If the ideal cutting profile for the respective type of sample has been performed by the operator one time and if it has been correspondingly stored, this cutting profile can be automatically used again any time without the operator having to drive the hand wheel anew. Thus, the ideal cutting profile can be used at any desired frequency such that great ease of use is achieved for the operator, and reproducibility of comparable cutting profiles is possible.

During rotation of the hand wheel, the encoder in particular detects positional data containing information on the respective position of the hand wheel. Based on these positional data, a control unit subsequently calculates the profile of the rotational movement and determines corresponding drive data or signals for the motor. In particular, the drive data or signals can be stored as the profile. The profile is also referred to as cutting profile or cutting speed profile as it is characteristic of the cutting movement.

In particular, the profile comprises a position profile, a speed profile and/or an acceleration profile, such that the cutting movement may be exactly repeated any desired number of times. In addition, the profile may include the respective cutting window. To this end, in particular a value for a lower limit and a value for an upper limit of the cutting window are stored such that the profile is adapted to the corresponding sample.

During generation of the first thin section the detected profile is not only stored, but also used for driving the motor in real-time in accordance with the detected profile, and thus for producing the first thin section. Thus, recording of the profile can be performed during the normal cutting operation and there is no need to carry out an additional rotational movement.

In a particularly preferred embodiment, a profile is recorded during production of a first thin section of a newly fed sample, and this stored profile is subsequently used for production of all the further thin section of said sample. Thus, for producing all thin section of a sample, the operator is required to manually operate the hand wheel only one time for producing the first thin section. All following thin sections are then automatically performed by the microtome using the profile determined by the operator.

It is further advantageous, if a plurality of profiles are detected by means of the encoder, and if these profiles are stored in a storage element. Thus, a plurality of possible cutting profiles is available such that a suitable profile can be selected for each type of sample. If a suitable profile has, however, not yet been stored, the operator must manually produce at least one thin section before the profile recorded during this process can be used for the production of further thin sections.

The profiles are in particular stored as a database, wherein preferably at least one characteristic feature is stored for each sample which is unambiguously assigned to the respective sample. In particular, the sample type and/or the sample size is stored as the characteristic feature. In addition, or as an alternative, information related to the respective operator can be stored. It is then possible to identify and select the profile suitable for a sample in a simple manner via this characteristic feature additionally stored.

In a particularly preferred embodiment the characteristic feature of a sample to be microtomed is determined upon feeding the sample, and said characteristic feature is compared with the characteristic features stored. Depending on the results of this comparison, one of the stored profiles is selected and the motor is driven in accordance with the selected profile when this sample is being microtomed. The advantage therein is that it is not necessary for the person operating the microtome to select the profile from a possibly long list of profiles because the microtome automatically selects the profile best suited for the sample to be microtomed.

In particular, the characteristic feature is determined via a barcode of the sample. For such barcode, information on the type of sample can be determined such that the profile best suited for the respective type of sample can be selected.

Preferably, a profile to be used for cutting a sample with the microtome is selected automatically. As an alternative, the operator may manually select one of the stored profiles for producing a thin section. To this end, the microtome includes an operating unit via which the operator is shown the various profiles stored and via which the operator may select one of such stored profiles. In particular, for each profile the operator is shown characteristic values of the respective profile such that it is easier for the operator to select the suitable profile.

In particular, the profile detected during rotation of the hand wheel is stored only if the microtome is operated in a recording mode. If the microtome is not operated in the recording mode, however, the motor is driven in accordance with the rotational movement of the hand wheel, but without storage of the detected profile. In an alternative embodiment, a corresponding profile may be stored during each manual rotation of the hand wheel.

In an automatic mode, the motor is driven in accordance with a previously stored profile, wherein a rotation of the hand wheel is not required to this end.

A further aspect of the present invention is related to a microtome for producing thin sections, comprising a sample holder for receiving the sample to be microtomed, a cutting unit for cutting the sample, a motor for generating a relative movement between the sample holder and the cutting unit for cutting the sample, and a hand wheel which is manually operable. Further, the microtome has an encoder for detecting a rotational movement of the hand wheel and a control unit for driving the motor. In a recording mode, the encoder detects a profile of a rotational movement performed for cutting a thin section. The detected profile is stored in a storage element by the control unit.

For producing at least one further thin section, the motor is driven by the control unit, after selection of a stored profile, in accordance with the stored profile selected.

Further features and advantages of the invention will be apparent from the following detailed description of exemplary embodiments thereof, taken in conjunction with the accompanying drawings, in which FIG. 1 is a schematic, perspective view of a microtome;

FIG. 3 is a schematic, perspective view of the hand wheel of the microtome of FIGS. 1 and 2;

FIG. 4 is a partial sectional side view of the hand wheel of FIG. 3.

FIG. 2 shows a top view thereof. A housing of the microtome 10 has been omitted here to allow better viewing of the interior components.

The microtome 10 comprises a sample holder 12 in which the sample to be microtomed can be clamped by means of a chuck 14. In particular, the sample to be microtomed consists of tissue samples embedded in paraffin, wherein a plurality of thin sections for examination using a microscope are to be cut from the respective tissue samples.

Figure 1:
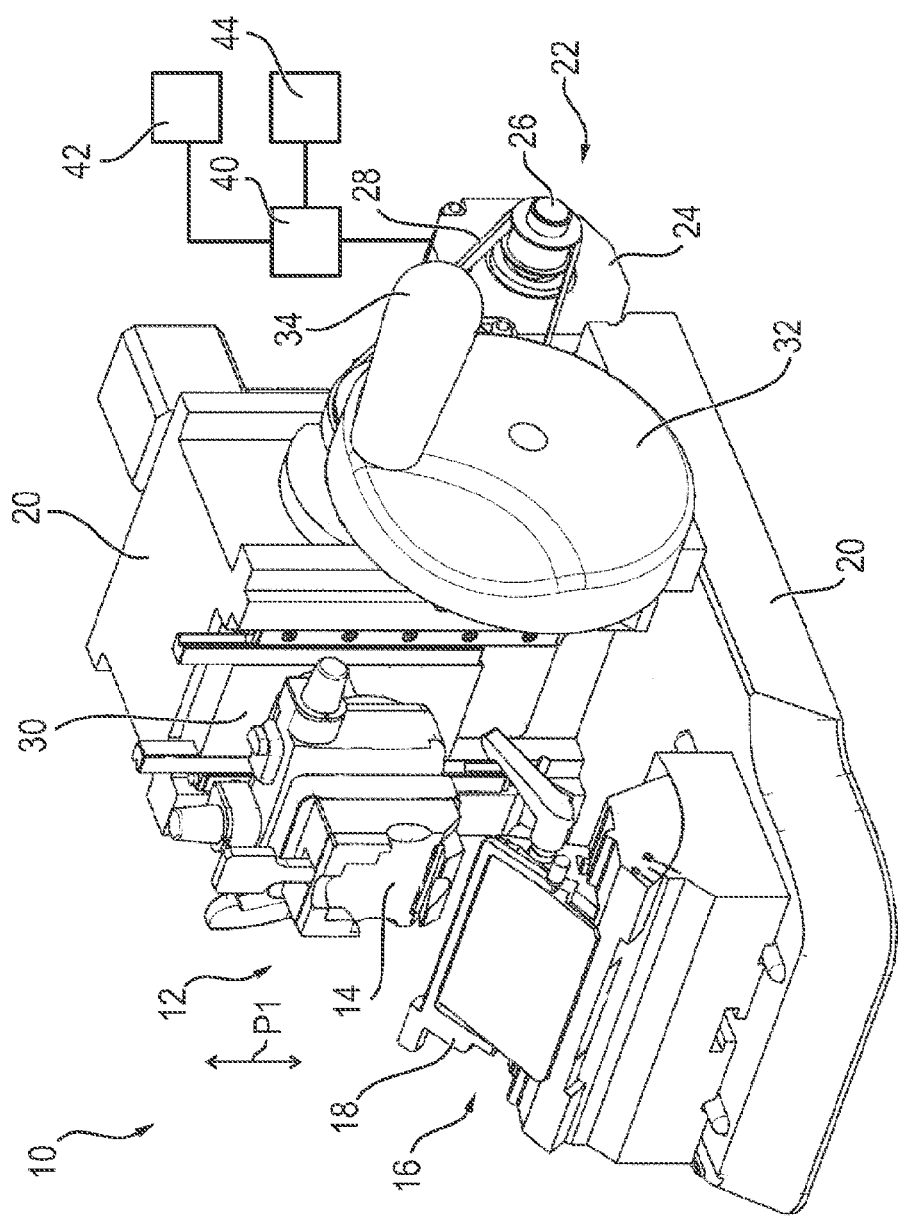
FIG. 1 shows a microtome 10 in a schematic perspective view.
Figure 2:
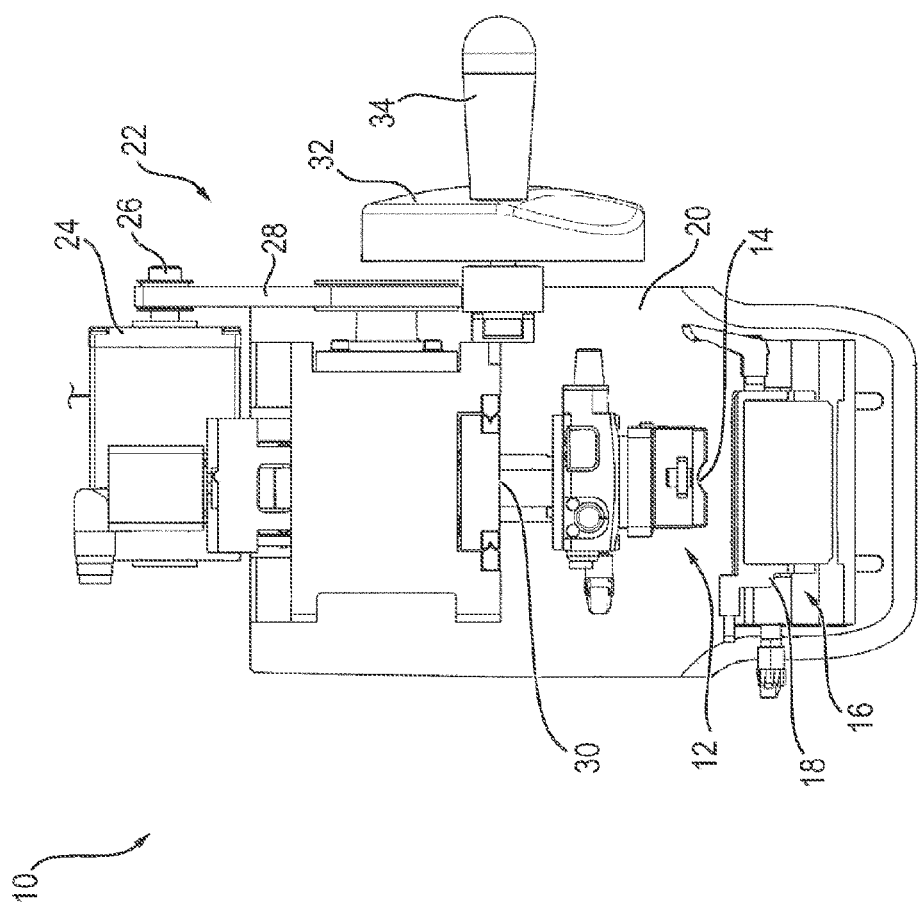
FIG. 2 is a top view of the microtome of FIG. 1.

Further, the microtome 10 comprises a cutting unit 16 which, in the embodiment shown in FIG. 1, is in the form of a blade holder 18 capable of holding a blade or knife.

The cutting unit 16 is stationary relative to the microtome frame 20, whereas the sample holder 12 is movable relative to the cutting unit 16 by means of a drive unit 22 in the direction of the double-headed arrow P1 in a reciprocating manner such that the sample received in the sample holder is cut by the cutting unit 16 as a result of this reciprocating movement, thus producing thin sections.

The drive unit 22 comprises a motor 24, the output shaft 26 thereof being connected via a tooth belt 28 with a coupling mechanism 30 via which in turn the sample holder 12 is moved relative to the cutting unit 16.

In an alternative embodiment of the invention, the motor 24 may be connected with the cutting unit 16 such that the latter is moved relative to the sample holder 12.

Moreover, the microtome 10 comprises a hand wheel 32 which has a handle 34 and can be manually operated by the user of the microtome 10 for producing thin sections. FIG. 3 shows a schematic perspective view, whereas FIG. 4 shows a partially sectional side view of the hand wheel 32.

The hand wheel 32 is supported on a shaft 36, wherein the shaft 36 is not coupled to the drive unit 22 for moving the sample holder 12. Instead, an encoder 38, in particular a rotary encoder, is used to detect rotational movement of the shaft 36, and thus rotational movement of the hand wheel 32. The signals and/or data generated by the encoder 38 as a function of the detected rotational movement of the hand wheel 32 are transmitted to a control unit 40 which converts the received data and/or signals into data and/or signals for driving the motor 24.

In particular, the encoder 38 detects positional data of the hand wheel 32, on the basis of which a profile of the cutting movement of the sample holder 12 relative to the cutting unit 14 is then determined. In particular this profile includes information on the cutting speed selected at each point of the cutting movement, on the accelerations, and on the respective position of the sample holder 12 relative to the cutting unit 16. In particular, the profile includes a position profile, a speed profile, and an acceleration profile which correspondingly represent the position, speed and acceleration, respectively, as a function of the time during performing the cutting movement, and which thus allow for exact reproduction of the cutting movement defined by the hand wheel 12. In particular, the profile is represented by the signal and/or data generated by the encoder 32, and or by the drive signals and/or data obtained by the control unit 40 therefrom.

Moreover, the determined profile further comprises information on the upper and lower limits of a cutting window to which the set cutting speed shall be applied. Such cutting window is dependent on the individual sample size, and must therefore be set individually for each sample.

Manual definition of the profile according to which the cutting movement is performed makes it possible that the profile can be individually adapted to the sample, and that the ideal cutting profile can thus be used for each sample. The selected cutting speed and accelerations are in particular dependent on the type and/or size of the sample.

According to the invention, in a recording mode, the profile for producing a thin section detected by the encoder 32 is stored in a storage element 42. This profile, once stored, can then be used as often as desired for producing further thin sections by selecting the profile and by the control unit 40 driving the motor 24 in accordance with the stored profile selected.

This is advantageous in that for each sample, or each type of sample, the operator must perform only one rotational movement of the hand wheel 32 for determining the ideal profile of the cutting movement when producing the first this section, and in that for production of the second thin section and any number of further thin sections, the once stored profile may be used wherein the operator must not drive the hand wheel 32. Thus, an ideal profile can be used for each sample or type of sample. Moreover, particularly simple handling of the microtome 10 is achieved because the operator is not required to rotate the hand wheel 32 for each thin section. Further, unlimited reproducibility of certain cutting profiles is guaranteed. A further advantage is the feature that the stored cutting profiles also include the upper and lower limits for the respective cutting window, and that therefore the skilled person is not required to individually set the cutting window.

Selection of a profile to be used may, for example, be manually achieved by the operator via the operating unit 44 of the microtome 10. As an alternative, selection of the stored profile can be accomplished automatically by the microtome 10 itself. For example, a barcode of a sample to be microtomed is scanned, through which barcode the characteristic features of the respective sample can be determined. The characteristic features determined are compared with stored characteristic features of these cutting profiles which have been unambiguously assigned to the respective cutting profiles, so that selection of the ideal cutting profile can be accomplished automatically. To this end, in particular the sample type and/or the sample identification unambiguously assigned to the stored profile are also stored in the storage element 42, such that when a further sample of the respective sample type is fed the respective cutting profile can be automatically selected through recognition of the respective sample type.

Alternatively, it is also possible, each time a new sample is fed to the sample holder 12, to manually produce the first thin section by the operator driving the hand wheel 32, with the corresponding profile of the cutting movement being detected and stored. Subsequently, the profile detected during production of the first thin section is used for producing at least a part, preferably all of the further thins section of the respective sample without requiring the operator to drive the hand wheel 32, In an alternative embodiment, different from that shown in FIGS. 1 to 4, a mechanical coupling may be provided between the shaft 36 of the hand wheel 32 and the sample holder 12. In this case, the encoder 38 may, for example, be integrated in the shaft 36 of the hand wheel 12 or in the output shaft 26 of the motor 24. In this embodiment, the microtome 10 is in particular formed such that it can be selectively driven either by a hand wheel 32 or by a motor 24.

Figure 5:
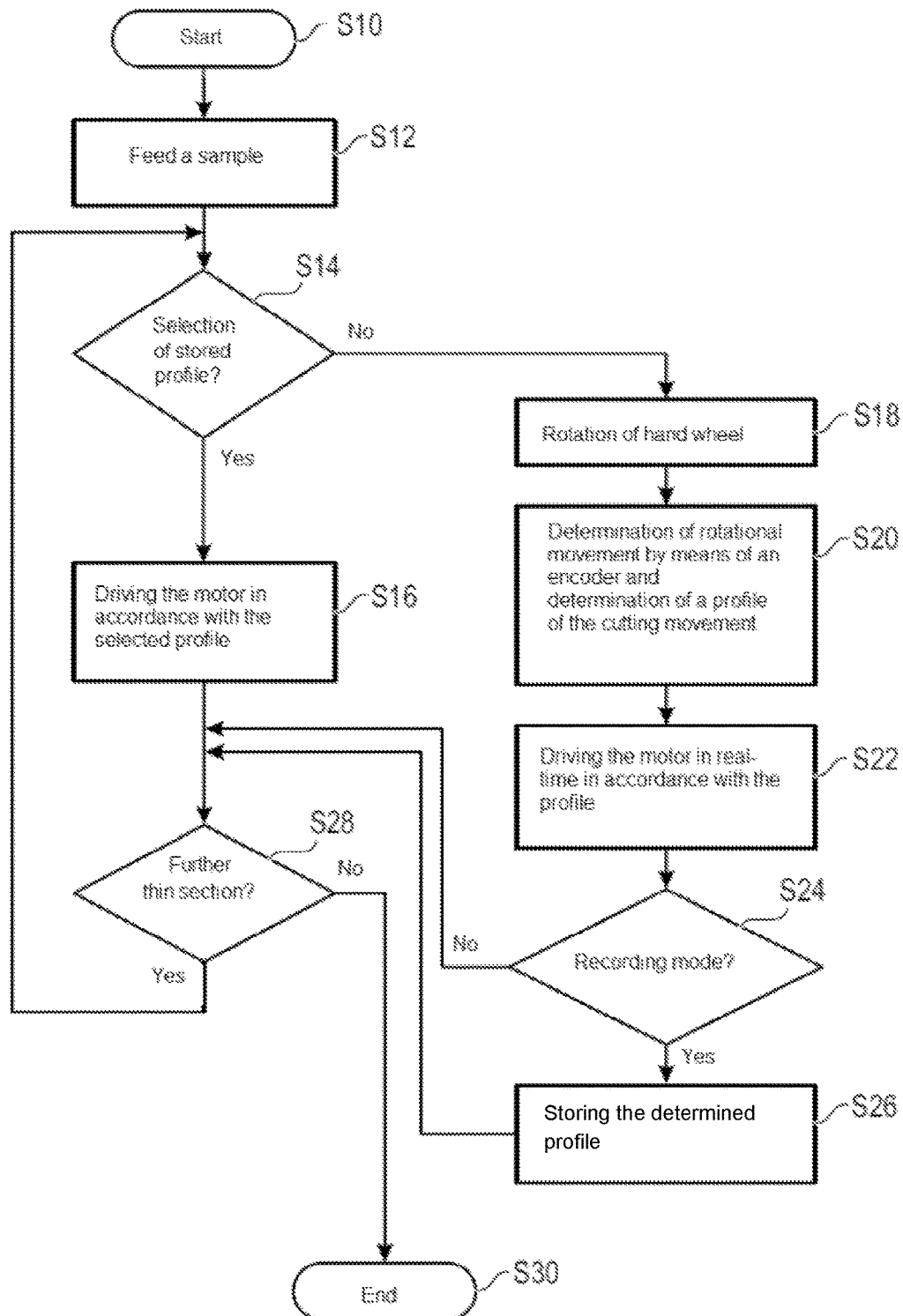
FIG. 5 is a flow chart showing a method of producing a thin section of a sample.

FIG. 5 shows a flow chart of a method of producing thin sections. After starting the process in step S10, a sample is fed to the sample holder 12 in step S12. In step S14, a profile previously stored in the storage element 42 can be selected. In particular, this can be accomplished automatically by the microtome 10, or manually by an operator. If one the profiles previously stored is selected in step S14, the motor 24 is driven in accordance with the stored, selected profile in step S16, and a thin section is produced thereby.

If, in contrast, none of the stored profiles is selected in step S14, or if no profile has been stored in the storage element 42 so far, the hand wheel 32 must be rotated in step S18 for producing a first thin section. During rotation of the hand wheel 32, the respective rotational movement is detected by means of the encoder 38, and a profile of this movement is determined. Herein, the motor 24 is driven in step S22 in real-time for detecting the profile corresponding to the profile of this first thin section In step S24, it is determined whether a recording mode is enabled. If so, the profile determined in step S20 is stored in the storage element 42 in step S26. In particular, further characteristic features, such as the sample type, the sample size, a sample identifier and/or the operator performing rotation of the hand wheel 32 are stored together with the profiles.

Following storage of the profile, it is determined in step S28 whether a further thin section is to be produced. If so, the process proceeds to step S14, i.e. it is again determined whether one of the stored profiles is to be used.

If, in contrast, no further thin section is to be produced the process ends in step S30.

If it is determined in step S24 that the recording mode has not been disabled the process directly proceeds to step S28, i.e. it is determined whether a further thin section is to be produced.

In an alternative embodiment of the invention, each time a rotation of the tooth wheel 32 is accomplished, i.e. each time a thin section is produced in real-time as a function of a manually defined profile, said profile may be automatically stored in the storage element 42. In this case, step S24 may be omitted because step S26, i.e. storage of the profile, is automatically carried out each time.

LIST OF REFERENCE SIGNS 10 microtome
12 sample holder 14 clutch
16 cutting unit
18 blade holder
20 microtome frame
22 drive unit
24 motor
26 output shaft
28 tooth belt
30 coupling mechanism
32 hand wheel
34 grip
36 shaft
38 encoder
40 control unit
42 storage element
44 operating unit
P1 direction
S10 bis S30 method step

The invention claimed is:

1. A method of producing thin sections by means of a microtome comprising:
    manually driving a hand wheel (32) for producing a first thin section, and
    detecting rotational movement of the hand wheel (32) during production of the first thin section with an encoder (38),
    determining a profile of the rotational movement, wherein the profile includes a position profile, a speed profile, an acceleration profile, a lower limit of a cutting window and/or an upper limit of a cutting window,
    storing the profile in a storage element (42),
    determining a plurality of the profiles with the encoder (38), said profiles being stored as a database in the storage element (42),
    storing at least one characteristic feature that is uniquely assigned to each of the profiles,
    selecting one of the stored profiles for producing at least a second thin section, wherein the characteristic feature of a sample is automatically determined for a sample to be microtomed, the determined characteristic feature is compared with the stored characteristic features, and one of the stored profiles is selected in dependence of the result of the comparison,
    and driving a motor (24) for producing the second thin section in accordance with the stored profile that is selected, wherein the motor (24) generates a cutting movement between a cutting unit (16) and a sample holder (12).

2. The method according to claim 1, wherein the motor (24) is driven in real-time in accordance with the profile detected by the encoder (38) for producing the first thin section.

3. The method according to claim 1, wherein the profile is recorded during production of the first thin section of a sample, and in that said stored profile is subsequently used for production of all further thin sections of the respective sample.

4. The method according to claim 1, wherein a type of the sample to be microtomed and/or a person operating the microtome (10) is stored as the characteristic feature.

5. The method according to claim 4, wherein the characteristic feature is determined via a barcode of the sample.

6. The method according to claim 1, wherein selection of one of the stored profiles for producing a thin section is manually accomplished.

7. The method according to claim 1, wherein, in a recording mode, a profile detected during rotation of the hand wheel (32) is stored, and wherein in an automatic mode, the motor (24) is driven in accordance with a prior stored, selected profile.

8. The method according to claim 1, wherein during production of the at least second thin section, the motor (24) is driven independently of the rotation of the hand wheel.

9. The method according to claim 1, wherein, during a revolution of the hand wheel (32), the encoder (38) outputs positional data including information on the respective position of the hand wheel (32), and wherein the profile of the cutting movement is detected in accordance with said positional data.

10. A microtome for producing thin sections, comprising:
    a sample holder (12) for receiving a sample to be microtomed,
    a cutting unit (16) for cutting the sample,
    a motor (24) for generating a relative movement between the sample holder (12) and the cutting unit (16) for cutting the sample,
    a manually operable hand wheel (32),
    an encoder (38) for detecting a rotational movement of the hand wheel (32), and
    a control unit (40) for driving the motor (24),
    characterized in that, in a recording mode, the control unit (40), using the encoder (38), determines a plurality of profiles of rotational movements (32) performed for cutting thin sections, wherein each of the profiles includes a position profile, a speed profile, an acceleration profile, a lower limit of a cutting window and/or an upper limit of a cutting window,
    the control unit (40) stores the profiles in a storage element (42),
    the control unit (40) stores for each profile at least one characteristic feature uniquely assigned thereto, and
    wherein the control unit (40), when producing at least one further thin section, automatically selects one of the stored profiles such that the control unit (40) determines a characteristic feature of the sample, compares the characteristic feature of the sample with the characteristic features of the profiles, automatically selects one of the profiles based on the comparison of the characteristic feature of the sample and the characteristic features of the profiles, and drives the motor (24) in accordance with the profile that is selected.

* * * * *